(12) United States Patent
Mattke et al.

(10) Patent No.: US 9,126,904 B2
(45) Date of Patent: Sep. 8, 2015

(54) PROCESS FOR PREPARING ISOCYANATES BY PHOSGENATION OF AMINES IN THE LIQUID PHASE

(71) Applicant: BASF SE, Ludwigshafen (DE)

(72) Inventors: Torsten Mattke, Freinsheim (DE); Markus Hiller, Maxdorf (DE); Hans-Juergen Pallasch, Kallstadt (DE)

(73) Assignee: BASF SE, Ludwigshafen (DE)

( * ) Notice: Subject to any disclaimer, the term of this patent is extended or adjusted under 35 U.S.C. 154(b) by 45 days.

(21) Appl. No.: 14/058,765

(22) Filed: Oct. 21, 2013

(65) Prior Publication Data

US 2014/0114087 A1   Apr. 24, 2014

Related U.S. Application Data

(60) Provisional application No. 61/717,651, filed on Oct. 24, 2012.

(51) Int. Cl.
*C07C 263/10* (2006.01)
(52) U.S. Cl.
CPC .................................. *C07C 263/10* (2013.01)

(58) Field of Classification Search
None
See application file for complete search history.

(56) References Cited

U.S. PATENT DOCUMENTS

| | | | |
|---|---|---|---|
| 7,584,629 B2 * | 9/2009 | Sohn et al. | 62/617 |
| 7,851,648 B2 * | 12/2010 | Sohn et al. | 560/347 |
| 2013/0060062 A1 | 3/2013 | Mattke et al. | |
| 2013/0109883 A1 | 5/2013 | Leschinski et al. | |

FOREIGN PATENT DOCUMENTS

| | | |
|---|---|---|
| EP | 1 575 904 | 12/2002 |
| WO | WO 2004/056758 | 7/2004 |
| WO | WO 2013/029918 A1 | 3/2013 |
| WO | WO 2013/060836 A1 | 5/2013 |

* cited by examiner

*Primary Examiner* — Karl J Puttlitz
(74) *Attorney, Agent, or Firm* — Oblon, McClelland, Maier & Neustadt, L.L.P.

(57) ABSTRACT

The present invention relates to a process for preparing isocyanates by reacting amines with phosgene in the liquid phase, where phosgene, hydrogen chloride and isocyanates are separated with stripping columns operated at different pressures.

8 Claims, 3 Drawing Sheets

PROCESS FOR PREPARING ISOCYANATES BY PHOSGENATION OF AMINES IN THE LIQUID PHASE

Figure 1:
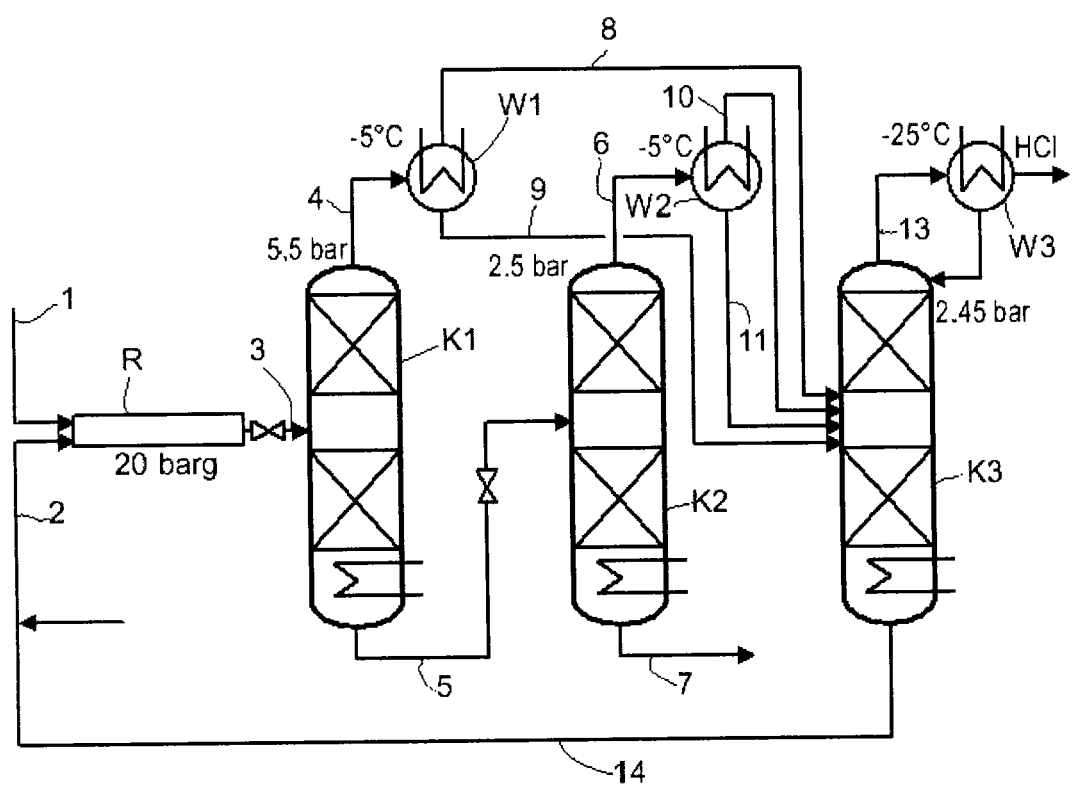

The invention relates to a process for preparing aromatic or aliphatic isocyanates by phosgenation of the corresponding amines in the liquid phase.

The liquid-phase phosgenation of amines as the classical route for preparing isocyanates has been described many times and is carried out on the industrial scale (see, for example, Ullmanns Enzyklopädie der Technischen Chemie, volume 7 (Polyurethane), 3rd revised edition, Carl Hanser Verlag, Munich-Vienna, p. 76 if (1993).). The aromatic isocyanates TDI (tolylene diisocyanate) and MDI (methylene di(phenyl isocyanate)) and also the aliphatic isocyanates hexamethylene diisocyanate (HDI) and isophorone diisocyanate (IPDI), in particular, are produced worldwide on an industrial scale.

Present-day industrial syntheses of the aromatic diisocyanates MDI and TDI and also the aliphatic diisocyanates HDI and IPDI are carried out virtually exclusively in continuous processes.

The reaction of the starting materials amine and phosgene is generally carried out in a number of stages. Such a multistage process with very high chemical yield, high space-time yield and low phosgene holdup is described in EP 1 575 904. According to that text, the reaction between an organic amine and phosgene is carried out in three or more stages, in an inert solvent, preferably toluene, chlorobenzene, dichlorobenzene or mixtures of the latter two, and using an excess of phosgene and a reduction in the pressure is carried out over each of the stages and the first phosgenation stage comprises a static mixer, preferably a nozzle, the second stage is carried out in a residence apparatus and the third stage is carried out in one or more (reaction) columns. The pressure upstream of the nozzle is preferably from 3 to 70 bar. The residence reactor of the second stage is preferably operated at a pressure of from 2.5 to 35 bar. Downstream of the nozzle, the reaction mixture is depressurized via a valve or another suitable device to the pressure of the second stage. However, the natural pressure drop of the nozzle or of the connection between nozzle and residence reactor can also be used for reducing the pressure. The reactor of the first stage, usually a static mixer, can also be integrated into the reactor of the second stage, a residence apparatus. The reactor of the third phosgenation stage, a reaction column, is preferably operated at a pressure of from 2 to 20 bar. Downstream of the reactor of the second stage, the reaction mixture is depressurized via a valve or another suitable device to the pressure of the reactor of the third stage. A natural pressure drop is optionally also sufficient for reducing the pressure.

The isocyanate-comprising product mixture which remains is subsequently passed to a further work-up (solvent removal, pure distillation). HCl obtained as by-product, excess phosgene and solvent residues are taken off as gaseous vapors from the reaction and distillation stages and passed to a thermal separation, e.g. as described in WO 2004056758.

The pressure decreases continually from mixing apparatus to residence reactor, to reaction column, to phosgene stripper and to HCl-phosgene separation. To avoid excessively high temperatures at the bottom of the phosgene stripper, which could adversely affect the yield, the pressure in this column is preferably kept very low (1 to 4 bar). The HCl-phosgene separation is coupled to this via the vapor stream and has to be operated at a slightly lower pressure. Appropriately low temperatures (−40 to −20° C.) are therefore necessary for the thermal separation of phosgene from the HCl stream. However, the refrigeration energy required for this leads to high capital and operating costs.

In view of this prior art, it was an object of the invention to provide an improved process for preparing isocyanates by liquid-phase phosgenation of the corresponding amines, which leads in a technically simple way to significant savings in capital and operating costs.

The object is achieved by a process for preparing isocyanates by reaction of amines with phosgene in the liquid phase, which comprises the following process stages:

a) mixing of a liquid amine-comprising starting material stream and a liquid phosgene-comprising starting material stream to give a feed stream, b) reaction of the feed stream from process stage a) in a residence reactor (R) to give a two-phase, gaseous/liquid reaction mixture which is fed either directly or after removal of the gaseous phase in a downstream separator (A) to a reaction column (K1), c) reaction of the two-phase, gaseous/liquid reaction mixture or only the liquid phase thereof in the reaction column (K1) to give an overhead stream and a bottom stream which is fed to a phosgene/hydrogen chloride stripping column, d) removal by distillation of phosgene and hydrogen chloride via the overhead stream from the phosgene/hydrogen chloride stripping column (K2), giving a bottom stream from the phosgene/hydrogen chloride stripping column (K2) which comprises the isocyanate and the solvent, from which, in process stage e) the desired isocyanate product is obtained by removal of the solvent by distillation and, in process stage, f) thermal separation of the vapor from the phosgene/hydrogen chloride stripping column (K2) in a separation column (K3) gives a hydrogen chloride-comprising vapor stream at the top and a bottom stream which comprises phosgene and solvent and is recycled to process stage (a), wherein the thermal separation in process stage f) is carried out at a pressure at the top of the separation column which is higher than the pressure at the top of the phosgene/hydrogen chloride stripping column.

It has surprisingly been found that the separation column in which hydrogen chloride is separated off at the top and phosgene is separated off via the bottom stream can be operated at a relatively high pressure and correspondingly relatively low temperatures, with corresponding energy savings for refrigeration.

A further advantage of a hydrogen chloride-phosgene separation at relatively high pressure is obtained when the hydrogen chloride has to be compressed for further processing, for example in an oxychloration process for preparing 1,2-dichloroethane.

In this case, the compression required and thus the corresponding capital and operating costs for the compressor are reduced.

The invention proceeds from a process for preparing isocyanates as described in EP 157 5904.

However, the separation column for the separation of hydrogen chloride and phosgene is operated at a pressure higher than that in the upstream phosgene/hydrogen chloride stripping column.

The phosgene/hydrogen chloride stripping column is, in particular, operated at a pressure at the top in the range from 1 to 4 bar gauge.

Preference is given to no device for actively reducing the pressure being provided between the phosgene/hydrogen chloride stripping column and the separation column.

The higher pressure at the top of the column compared to the phosgene/hydrogen chloride stripping column is preferably achieved by the overhead stream from the phosgene/hydrogen chloride stripping column or a vapor stream obtained together with a condensate stream by partial condensation of the overhead stream from the phosgene/hydrogen chloride stripping column in a condenser (W2) being compressed in an ejector (E) before being fed to the separation column so as to give a stream which is introduced into the separation column (K3).

The process is not restricted with regard to the isocyanates which can be produced thereby. The isocyanates can preferably be the aromatic isocyanates TDI (tolylene diisocyanate) and MDI (methylene di(phenyl isocyanate)) and also the aliphatic isocyanates hexamethylene diisocyanate (HDI) and isophorone diisocyanate (IPDI).

As driving stream for the ejector, use is made of, in particular, the overhead stream from the reaction column (K1) or the gas phase of the partially condensed overhead stream from the reaction column, preferably the gas phase of the partially condensed overhead stream from the reaction column (K1).

In particular, the vapor stream which is obtained in addition to a liquid stream, which is fed to the reaction column (K1), from the gaseous/liquid reaction mixture from the residence reactor (R) in the downstream separator (A) is utilized as driving stream for the ejector (E).

Furthermore, the condensate stream which is obtained by partial condensation of the overhead stream from the phosgene/hydrogen chloride stripping column (K2) in the condenser is preferably compressed in a further ejector to give a condensate stream which is introduced into the separation column, with the ejector utilizing, as driving stream, the condensate stream which is obtained in addition to the vapor stream after partial condensation of the overhead stream from the reaction column in the condenser. However, the condensate stream from the partial condensation of the overhead stream from the phosgene/hydrogen chloride stripping column can be conveyed by means of a pump into the separation column which operates at a higher pressure at the top.

In a further variant, the higher pressure at the top of the separation column compared to the phosgene/hydrogen chloride stripping column is achieved by the overhead stream from the phosgene/hydrogen chloride stripping column or a vapor stream which is obtained in addition to a condensate stream by partial condensation of the overhead stream from the phosgene/hydrogen chloride stripping column in a condenser being compressed, before being introduced into the separation column, in an ejector to give a stream which is introduced into the separation column, with the ejector utilizing, as driving stream, the vapor stream which is taken off from the reaction mixture of the residence reactor or a downstream separator.

The gas offtake from the residence reactor or an optionally downstream separator can preferably be followed by a gas scrub using solvent for separating off residual traces of isocyanate.

The invention is illustrated below with the aid of a drawing and examples.

Figure 2:
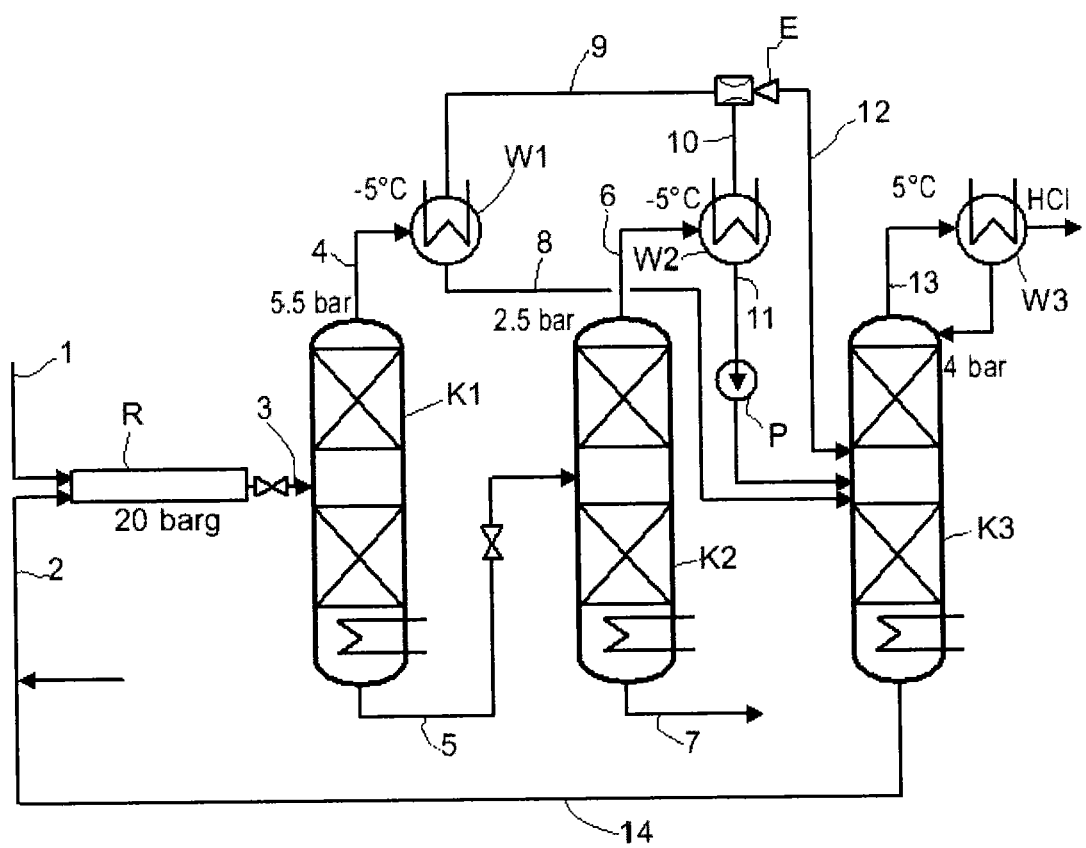
Figure 3:
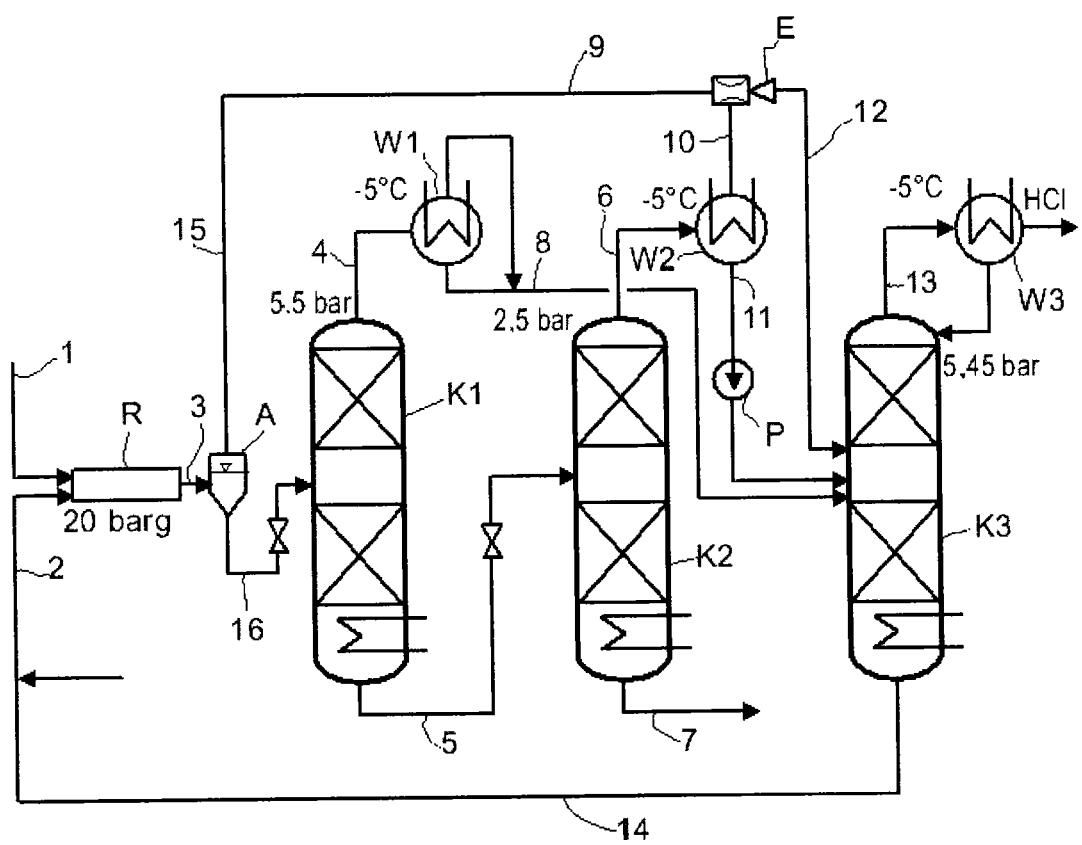

In the individual drawings:

FIG. 1 schematically shows a plant for preparing isocyanates by liquid-phase phosgenation of amines according to the prior art, FIG. 2 schematically shows a preferred embodiment of a plant for carrying out the process of the invention and FIG. 3 schematically shows a further preferred plant for carrying out the process of the invention.

In the figures, identical reference symbols in each case denote identical or corresponding features.

The plant shown in FIG. 1 for carrying out a liquid-phase phosgenation according to the prior art comprises a residence reactor R to which an amine-comprising stream 1 and a phosgene-comprising stream 2 are fed. The reaction mixture 3 from the residence reactor R is fed to a reaction column K1 and there separated into an overhead stream 4 and a bottom stream 5. The overhead stream 4 is separated in a first condenser W1 into a vapor stream 9 and a condensate stream 8 which are each fed to a separation column K3. The bottom stream 5 from the reaction column K1 is fed to a phosgene/hydrogen chloride stripping column K2 and separated therein into a stream 6 which is separated in a second condenser W2 into a vapor stream 10 and a condensate stream 11, which are each fed to the separation column K3, and also a bottom stream 7 which comprises the isocyanate and solvent and from which the isocyanate is obtained by removal of the solvent by distillation in an apparatus not shown in the figure. In the separation column K3, an overhead stream 13, which is partially condensed in a third condenser W3, and also a bottom stream 14, which is recycled to the process, are taken off.

The scheme shown in FIG. 2 of a preferred plant according to the invention comprises, compared to the plant according to the prior art shown in FIG. 1, an ejector E in which the vapor stream 10 which is obtained from the overhead stream 6 from the phosgene/hydrogen chloride stripping column K2 in the second condenser W2 is compressed by means of the vapor stream 9 which is obtained by partial condensation of the overhead stream 4 from the reaction column K1 in the first condenser W1 to give a stream 12 which is fed to the separation column K3. In the preferred variant shown in FIG. 2, the condensate stream 11 which is obtained by partial condensation of the overhead stream 6 from the phosgene/hydrogen chloride stripping column K2 in the second condenser W2 is fed by means of a pump P to the separation column K3.

FIG. 3 schematically shows a further preferred embodiment of a plant for carrying out the process of the invention, according to which the ejector E is, in contrast to the variant shown in FIG. 2, operated by means of a gaseous driving stream 15 which is obtained in addition to a liquid stream 16, which is fed to the reaction column K1, from the reaction mixture 3 from the residence reactor R in a separator. Compared to the plant shown in FIG. 2, the overhead stream 9 from the first condenser W1 is not fed as driving stream to the ejector E but instead introduced into the separation column K3.

COMPARATIVE EXAMPLE

In a plant corresponding to that depicted in FIG. 1 for preparing tolylene diisocyanate, an amine-comprising stream 1 and a phosgene-comprising stream 2 are mixed at about 20 bar in a residence reactor R and the amine reacts in the residence reactor R to form the corresponding isocyanate and HCl. In the subsequent reaction column K1, intermediates optionally formed (carbamoyl chlorides) are thermally dissociated into the isocyanate and HCl at 5.5 bar.

HCl and excess phosgene are taken off via the overhead stream 4 from the reaction column K1. The bottom stream 5 from the reaction column K1 is fed to a phosgene/hydrogen chloride stripping column K2 in which residual traces of HCl and phosgene and also parts of the solvent are taken off at 2.5 bar. The bottom stream 7 from the phosgene/hydrogen chloride stripping column K2 is largely free of phosgene and HCl. The overhead streams from the two columns K1 and K2, stream 4 and stream 6, which comprise essentially HCl, phosgene and solvent, are each partially condensed at −5° C. in downstream condensers, W1 and W2. The condensate streams 9 and 11 and the residual vapors, streams 8 and 10, are subsequently fed to a further separation column K3 for separation of HCl and phosgene at 2.45 bar. Here, a condensate temperature of −25° C. has to be achieved in the condenser W3 at the top of the separation column K3.

EXAMPLE 1

According to the Invention

In the plant shown in FIG. 2, the residual vapor 10 from the phosgene/hydrogen chloride stripping column K2 is compressed to a pressure of 4 bar in a driving jet nozzle E (ejector) by means of the residual vapor 8 from the reaction column K1 and fed to the separation column K3. This can be operated at 4 bar instead of 2.45 bar as in the comparative example. The condensate from the phosgene/hydrogen chloride stripping column K2 is likewise brought to 4 bar by means of a pump P. Due to the increased column pressure, the condensation temperature for the vapor stream 13 from the separation column K3 rises to −5° C. The low-temperature condensation at −25° C. required in the comparative example becomes unnecessary in this case and is replaced by refrigeration at a higher and therefore cheaper level.

EXAMPLE 2

According to the Invention

In the plant shown in FIG. 3, the high-pressure gas phase formed in the residence reactor R is utilized for compressing the residual vapor from the phosgene/hydrogen chloride stripping column K2. For this purpose, a separator A in which the gas phase and liquid phase are separated has to be provided before the depressurization of the reaction mixture 3 into the reaction column K1. The residual vapor from the phosgene/hydrogen chloride stripping column K2 can be compressed to 5.5 bar by means of the high-pressure gas phase, stream 15. Correspondingly, the condensation temperature for the vapor stream 13 from the separation column K3 rises to about 5° C. The pressure at the top of the separation column K3 is 5.5 bar.

The pressures indicated in the examples are absolute pressures.

The invention claimed is:

1. A process for preparing isocyanates by reaction of amines with phosgene in the liquid phase, the process comprising:
 a) mixing a liquid amine-comprising starting material stream and a liquid phosgene-comprising starting material stream to obtain a feed stream,
 b) reacting the feed stream from process stage a) in a residence reactor to give a two-phase, gaseous/liquid reaction mixture which is fed either directly or after removal of the gaseous phase in a downstream separator to a reaction column,
 c) reacting the two-phase, gaseous/liquid reaction mixture or only the liquid phase thereof in the reaction column to give an overhead stream and a bottom stream which is fed to a phosgene/hydrogen chloride stripping column,
 d) removing by distillation of phosgene and hydrogen chloride via the overhead stream from the phosgene/hydrogen chloride stripping column, to obtain a bottom stream from the phosgene/hydrogen chloride stripping column which comprises the isocyanate and the solvent, from which,
 e) the desired isocyanate product is obtained by removing the solvent by distillation and, and
 f) performing thermal separation of a residual vapor from the phosgene/hydrogen chloride stripping column in a separation column to obtain a hydrogen chloride-comprising vapor stream at the top and a bottom stream which comprises phosgene and solvent and is recycled to the mixing a),
 wherein the thermal separation f) is carried out at a pressure at the top of the separation column which is higher than the pressure at the top of the phosgene/hydrogen chloride stripping column,
 and wherein
 the higher pressure at the top of the separation column compared to the phosgene/hydrogen chloride stripping column is achieved by:
 a first ejector for the overhead stream from the phosgene/hydrogen chloride stripping column or a vapor stream obtained together with a condensate stream by partial condensation of the overhead stream from the phosgene/hydrogen chloride stripping column in a second condenser, and/or
 a further ejector which compresses the condensate stream which is obtained by partial condensation of the overhead stream from the phosgene/hydrogen chloride stripping column in the second condenser.

2. The process according to claim 1, wherein the higher pressure at the top of the separation column compared to the phosgene/hydrogen chloride stripping column is achieved by the overhead stream from the phosgene/hydrogen chloride stripping column or a vapor stream obtained together with a condensate stream by partial condensation of the overhead stream from the phosgene/hydrogen chloride stripping column in a second condenser being compressed in an ejector before being fed to the separation column so as to give a stream which is introduced into the separation column.

3. The process according to claim 2, wherein the overhead stream from the reaction column or the gas phase of the partially condensed overhead stream from the reaction column, preferably the gas phase of the partially condensed overhead stream from the reaction column, is utilized as driving stream for the ejector.

4. The process according to claim 2, wherein the vapor stream which is obtained in addition to a liquid stream, which is fed to the reaction column, from the gaseous/liquid reaction mixture from the residence reactor in the downstream separator is utilized as driving stream for the ejector.

5. The process according to claim 3, wherein the condensate stream which is obtained by partial condensation of the overhead stream from the phosgene/hydrogen chloride stripping column in the second condenser is compressed in a further ejector to give a condensate stream which is introduced into the separation column, with the further ejector utilizing, as driving stream, the condensate stream which is obtained in addition to the vapor stream after partial condensation of the overhead stream from the reaction column in the first condenser.

6. The process according to claim 4, wherein the gaseous/liquid reaction mixture from the residence reactor or the vapor stream which is obtained in the downstream separator is subjected to a gas scrub using a solvent in order to separate off residual traces of isocyanate.

7. The process according to claim 1, wherein the pressure at the top of the phosgene/hydrogen chloride stripping column is in the range from 1 to 4 bar gauge.

8. The process according to claim 1, wherein the pressure at the top of the phosgene/hydrogen chloride stripping column is lower than the pressure at the top of the separation column.

* * * * *